United States Patent
Litwak et al.

(10) Patent No.: US 6,929,777 B1
(45) Date of Patent: Aug. 16, 2005

(54) PNEUMATICALLY ACTUATED INTEGRATED LIFE SUPPORT SYSTEM

(75) Inventors: Philip Litwak, Pittsburgh, PA (US); Mark J. Gartner, Wexford, PA (US)

(73) Assignee: Ension, Inc., Pittsburgh, PA (US)

( * ) Notice: Subject to any disclaimer, the term of this patent is extended or adjusted under 35 U.S.C. 154(b) by 453 days.

(21) Appl. No.: 10/206,637

(22) Filed: Jul. 26, 2002

Related U.S. Application Data

(60) Provisional application No. 60/308,087, filed on Jul. 26, 2001.

(51) Int. Cl.$^7$ .......................... A61M 1/36; A61M 37/00; F04B 23/14
(52) U.S. Cl. ...................... 422/45; 604/6.11; 604/6.14; 261/DIG. 28
(58) Field of Search .............................. 604/4.01, 6.11, 604/6.14, 5.01, 19, 23, 24, 93.01, 131, 140–1, 604/149–50; 422/44–5, 48; 261/2, 3, 19–22, 261/24, 28–30, 34.1, 35, 36.1, 37–8, 64.1, 261/64.4, 75, 83–7, 94, 95, 101–102, DIG. 28

(56) References Cited

U.S. PATENT DOCUMENTS

| | | | | |
|---|---|---|---|---|
| 3,237,565 A | * | 3/1966 | Hartland | 415/116 |
| 3,374,743 A | * | 3/1968 | Stutely et al. | 417/65 |
| 4,018,859 A | * | 4/1977 | Muller | 261/87 |
| 4,366,051 A | * | 12/1982 | Fischel | 210/96.2 |
| 5,795,504 A | * | 8/1998 | Berchotteau | 261/30 |
| 5,851,443 A | * | 12/1998 | Rajendren | 261/87 |
| 6,074,554 A | * | 6/2000 | Ray et al. | 210/194 |
| 6,106,776 A | | 8/2000 | Borovetz et al. | |
| 6,217,826 B1 | | 4/2001 | Reeder et al. | |
| 6,348,175 B1 | | 2/2002 | Borovetz et al. | |

* cited by examiner

Primary Examiner—Patricia Bianco
(74) Attorney, Agent, or Firm—BLK Law Group; Blynn L. Shideler; Krisanne Shideler

(57) ABSTRACT

A fluid pump used to circulate and oxygenate blood, the fluid pump having an electrical or pneumatic motor having a motor shaft, a gas exchange assembly connected to one end of the motor shaft, and a hollow venturi that defines a venturi inlet opening, a venturi exhaust opening, and a venturi suction opening, wherein the venturi suction opening is fluidly connected to the gas exchange assembly to aspirate carbon dioxide rich gas.

16 Claims, 2 Drawing Sheets

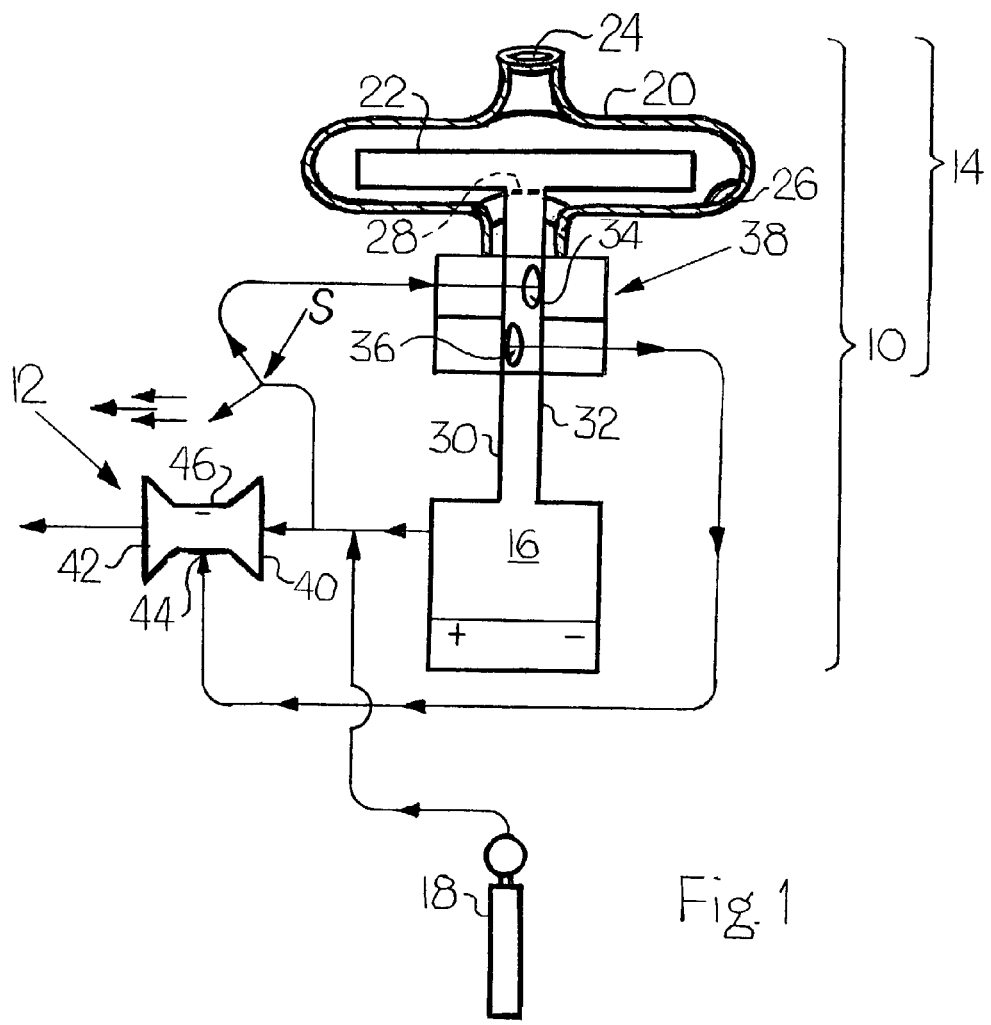
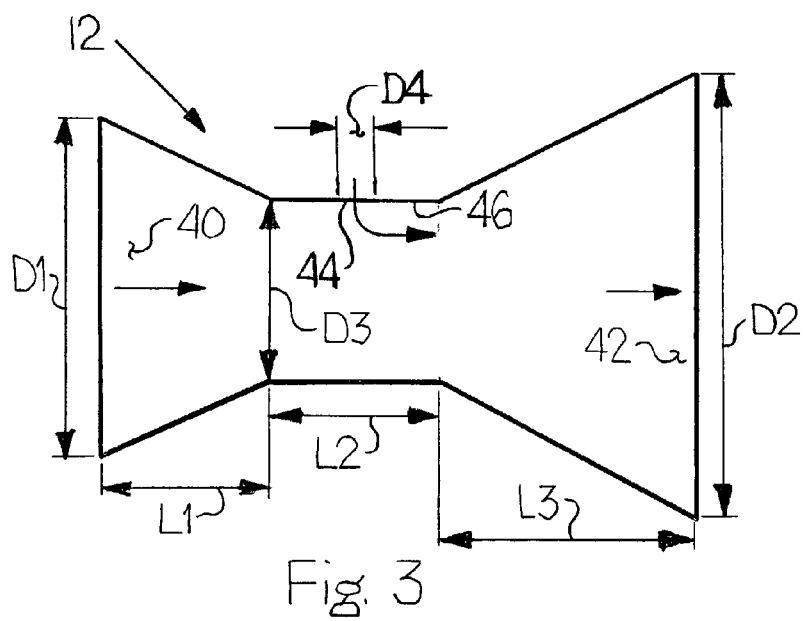
Fig. 1
Fig. 3

PNEUMATICALLY ACTUATED INTEGRATED LIFE SUPPORT SYSTEM

CROSS-REFERENCE TO RELATED APPLICATION

This application claims the benefit of earlier filed U.S. Provisional Patent Application Ser. No. 60/308,087, filed Jul. 26, 2001, entitled "Pneumatically Actuated Integrated Life Support System."

BACKGROUND OF THE INVENTION

1. Field of the Invention

The present invention generally relates to a fluid pump and, more particularly, to a blood pump and blood oxygenator.

2. Brief Description of the Prior Art

Approximately one percent of medical evacuation emergency transport systems in the United States are capable of transporting patients who require extracorporeal membrane oxygenation (hereinafter "ECMO") or cardipulmomary bypass (hereinafter "CPB"). This small percentage can be directly linked to the physical size, weight, and robustness of conventional portable ECMO and CPB systems. Size and weight of portable systems are important limitations, primarily due to a limited amount of space in a conventional ambulance, aircraft, or helicopter or the limited cargo capacity of an aircraft or helicopter.

In those ECMO and CPB systems which are used in connection with medical evacuation emergency transport, blood is pumped via an electric motor energized by battery power. Although electric motors are widely used and are generally acceptable, unreliable discharge characteristics of rechargeable batteries and faulty charging methods can cause the ECMO and CPB systems to sometimes function in unpredictable ways.

Therefore, a need exists for a fluid pump, such as for liquid blood, which is more compact than known blood pumps, weighs less than known blood pumps, simultaneously oxygenates/decarbonates the liquid blood via a compressed gaseous fluid source, and may include a motor simultaneously actuated by the compressed gaseous fluid source.

SUMMARY OF THE INVENTION

The present invention helps to solve the inadequacies of the prior art through a fluid pump used to circulate and simultaneously oxygenate/decarbonate blood. The fluid pump generally includes a motor having a motor shaft, a fluid exchange assembly connected to one end of the motor shaft, and a hollow venturi that defines a venturi inlet opening, a venturi exhaust opening, and a venturi suction opening, wherein the venturi suction opening is fluidly connected to the fluid exchange assembly.

A compressed fluid source is fluidly connected to the venturi inlet opening. The motor may be electrically actuated via rechargeable batteries electrically connected to the motor. Preferably, however, the motor is a pneumatically actuated (using a gas mixture principally comprised of oxygen) motor having a motor housing that defines a motor gas inlet and a motor gas outlet, wherein the motor gas outlet is fluidly connected to the venturi inlet opening.

A speed reducer may be connected to the motor shaft between the motor shaft and the fluid exchange assembly, and the compressed fluid source may be fluidly connected to the motor gas inlet, wherein the compressed fluid source is an E-size cylinder of oxygen or an oxygen containing gas.

The fluid exchange assembly includes a housing that defines a blood inlet and a blood outlet, a fiber-based or porous distributor disk surrounded by the housing, a double lumen shaft connected to the fiber-based distributor disk, and a gas plenum connected to the double lumen shaft.

In summary, the first and second embodiments of the present invention can be used to aspirate a fluid, such as an oxygen enriched gas mixture into the fluid exchange assembly. In the second preferred embodiment, the compressed fluid source can also drive the pneumatic motor and produce results which are nearly identical to the results obtained from the first embodiment having an electric motor. However, the second embodiment fluid pump can be made approximately fifty percent lighter than the first embodiment and approximately eighty percent smaller.

These and other advantages of the present invention will be clarified in the description of the preferred embodiment taken together with the attached drawings in which like reference numerals represent like elements throughout.

BRIEF DESCRIPTION OF THE DRAWINGS

FIG. 1 is a schematic view of one embodiment of the present invention;

FIG. 3 is a side view of one embodiment of a venturi according to the present invention.

DETAILED DESCRIPTION OF THE INVENTION

Figure 2:
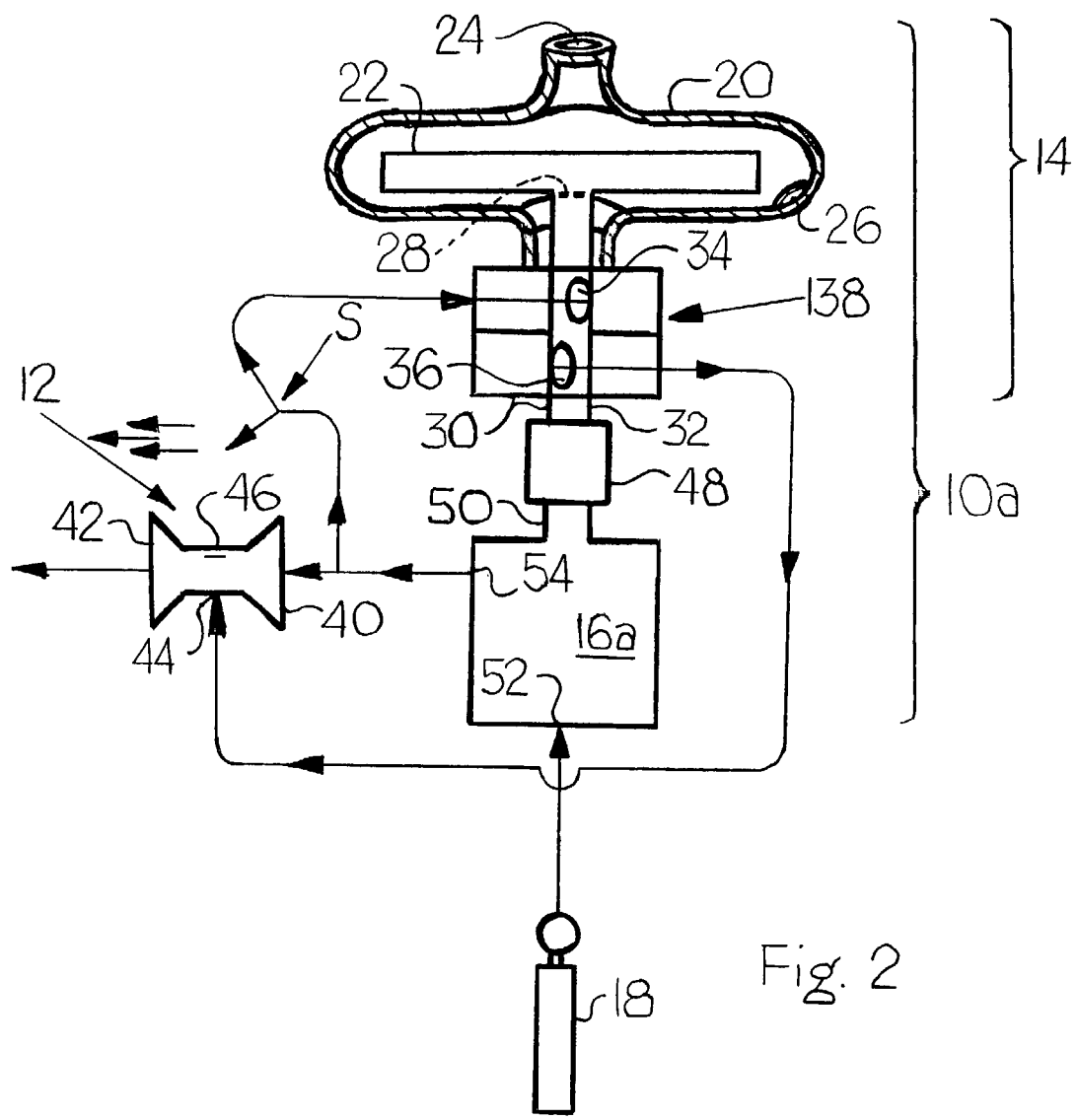
FIG. 2 is a schematic view of a second preferred embodiment of the present invention.

This application claims the benefit of U.S. Provisional Patent Application Ser. No. 60/308,087, herein incorporated by reference in its entirety.

FIG. 1 shows a blood/pump oxygenator 10, 10A and venturi 12 according to a first embodiment of the present invention. FIG. 2 shows a blood/pump oxygenator 10A according to a second and preferred embodiment of the present invention. FIG. 3 shows the venturi 12 shown in FIGS. 1 and 2.

The blood pump/oxygenators 10, 10A shown in FIGS. 1 and 2 generally include a fluid exchange assembly 14, a motor 16, a compressed fluid source 18, and the venturi 12. The fluid exchange assembly 14 and associated electric motors are described in great detail in U.S. Pat. Nos. 6,348,175; 6,217,826; and 6,106,776, all herein incorporated by reference in their entirety. In general, however, the fluid exchange assembly includes a fluid exchange housing which surrounds one or more hollow fiber-based distributor disks 22. The fluid exchange housing 20 defines a venous blood inlet 24, an arterial blood outlet 26, and is preferably made from a biocompatible material, such as polycarbonate. The one or more fiber-based distributor disks are connected to one end 28 of a double lumen shaft 30, and the other end 32 of the double lumen shaft 30 is connected to the motor 16. The double lumen shaft 30 defines a shaft inlet 34 and a shaft outlet 36, with the shaft inlet 34 and shaft outlet 36 fluidly separated from one another by a rotating gas plenum 38.

As shown in FIGS. 1–3, the first and second embodiments of the present invention further include the hollow venturi 12. The venturi 12 generally defines a venturi inlet opening 40, a venturi exhaust opening 42, and a venturi suction opening 44. In one preferred embodiment, as shown in FIG. 3, the venturi inlet opening 40 preferably has an internal diameter D1 of approximately 1.1 cm and a venturi exhaust internal diameter D2 opening of approximately 1.7 cm. The venturi inlet opening tapers a distance L1 of approximately 2 cm to one end of a throat 46, with the throat 46 having an internal diameter D3 of approximately 0.8 cm, a length L2 of approximately 1 cm, and a cross-sectional flow area of approximately 2 cubic centimeters. The venturi suction opening 44 is defined along the length L2 of the throat 46, with the venturi suction opening 44 having an internal diameter D4 of approximately 0.3 cm. The venturi exhaust opening 42 also tapers a distance L3 of approximately 3 cm toward the other end of the throat 46.

Although FIG. 3 represents the preferred venturi 12 embodiment, other venturi 12 dimensions can be obtained using well-known fluid design theories. For example, if fluid speed is sufficiently subsonic, with V<0.3 Mach, Bernoulli's equation can be used to predict fluid flow. Ignoring potential energy differences and viscous losses yields:

$$P_A - P_B = \Delta P = \tfrac{1}{2}\rho V_B^2 - \tfrac{1}{2}\rho V_A^2 \qquad [1]$$

Using Equation [1] and the equation of continuity, throat velocity $V_B$ can be expressed as:

$$\Delta P = \tfrac{1}{2}\rho V_A^{2} * [(A_A/A_B)^2 - 1] \qquad [2]$$

Solving for upstream velocity $V_A$ and multiplying by the cross-sectional area $A_A$ gives the volumetric flow rate Q:

$$Q = \sqrt{2P} * [A_A / \sqrt{(A_A/A_B)}] \qquad [3]$$

Equation [3] is then multiplied by a discharge coefficient C of approximately 0.90–0.98 to account for viscosity of fluids. The discharge coefficient C is found to depend on the Reynolds number of the flow.

The function of the venturi 12 is to aspirate an oxygen rich gas mixture into the fluid exchange assembly 14 to affect oxygenation/decarbonation. Therefore, knowing the total gas-side pressure drop of the pump-oxygenator system permits the estimation of the required pressure differential to generate a desired flow rate of sweep gas through the venturi 12. That is, for a required gas-side pressure drop, Equation [3] and the discharge coefficient can be used to predict requisite venturi 12 geometry.

Referring again to FIG. 1, the motor 16 in the first embodiment of the present invention includes an electrically-actuated motor 16 powered by rechargeable batteries. The compressed fluid source 18 is fluidly connected to the venturi inlet opening 42. In this first embodiment, the venturi suction opening 44 is fluidly connected to the fluid exchange assembly 14 via the shaft outlet 36 defined by the double lumen shaft 30.

In operation of the first embodiment blood pump/oxygenator 10, compressed gas flows from the compressed fluid source 18 into the venturi inlet opening 42 and simultaneously through bleed valve S into the shaft inlet 34 of double lumen shaft 30. As the compressed gas accelerates through the throat 46 of the venturi 12, the pressure drop creates a suction that draws carbon dioxide rich gas from the shaft outlet 36 of the double lumen shaft 30 and evacuates the carbon dioxide rich gas through the venturi exhaust opening 42. Simultaneously, gas enriched with oxygen, carbon dioxide or other gaseous elements flows through the shaft inlet 34 of the double lumen shaft 30 and travels to the gas exchange fiber distribution disks 22.

The first embodiment blood/pump oxygenator 10 represents an advancement in the art because blood is directly oxygenated while carbon dioxide rich gas is drawn away from the fluid exchange assembly 14 by the venturi 12.

However, the second embodiment 10A of the present invention represents the preferred embodiment.

The second and preferred embodiment 10A of the present invention is similar to the first embodiment 10, with like reference numerals indicating like parts. However, as shown in FIG. 2, the motor 16A in the second embodiment is a pneumatic motor, such as the MMR-0700 Model pneumatic motor commercially available from Micro Motors, Inc., Santa Ana, Calif.; moreover, the compressed fluid source 18 is fluidly connected to the pneumatic motor 16A as well as the venturi 12 and fluid exchange assembly 14. The pneumatic motor mentioned above tested has a consumption rate of approximately 1.6 cubic feet per minute and generates approximately 9.3 ounce-inch of torque at 1750 RPM. The compressed fluid source 18 is preferably an E-sized cylinder containing approximately 25 cubic feet of gaseous fluid and an operating pressure of approximately 2250 psi.

Because the pneumatic motor 16A is powered by a compressed fluid source 18 having a finite size, a speed reducer 48 or gear head may be added between a motor shaft 50 and the gas plenum 38 to reduce motor 16A speed. It has been found that using a speed reducer, such as a Sterling Instrument model S9118A, will reduce motor speed but still allow adequate torque. The purpose of the speed reducer 48 is to achieve a useful cylinder life of approximately thirty minutes. Without the speed reducer 48, cylinder life is approximately fifteen minutes with the MMR-0700 Model pneumatic motor. It is noted that blood flow rate is increased by faster rotation of the motor shaft 50, and an increase in motor shaft 50 rotation requires higher pressure gas. Therefore, a greater pressure differential can also be created in the venturi throat 46 to aspirate oxygen rich gas into the shaft inlet 34 and pull carbon dioxide enriched gas from the shaft outlet 36 of the double lumen shaft 30 at a greater rate.

With continuing reference to FIG. 2, a compressed fluid, such as oxygen rich gas, flows into the pneumatic motor 16A through a motor gas inlet 52, and low pressure gas escapes through a motor gas outlet 54. The escaped gas flows simultaneously through the venturi inlet opening 40 and the shaft inlet 34 of the double lumen shaft 30. Therefore, the compressed gas can be used to power the pneumatic motor 16A, provide oxygenated gas to the fiber-based distributor disks 22, and simultaneously draw carbon dioxide enriched gases through the shaft outlet 36. The primary benefits of this design are the elimination of occasionally unreliable batteries and a decrease in the overall size and weight of the blood pump/oxygenator 10A.

The present invention can be used to mix two similar or dissimilar fluids and is not limited to oxygen and carbon dioxide blood transfers.

The invention has been described with reference to the preferred embodiment. Obvious modifications and alterations will occur to others upon reading and understanding the preceding detailed description. It is intended that the invention be construed as including all such modifications and alterations insofar as they come within the scope of the appended claims or the equivalents thereof.

We claim:

1. A fluid pump used to circulate a first fluid with a second fluid, the fluid pump comprising:
    a motor having a motor shaft;
    a fluid exchange assembly connected to one end of the motor shaft; and
    a hollow venturi that defines a venturi inlet opening, a venturi exhaust opening, and a venturi suction opening, wherein the venturi suction opening is fluidly connected to the fluid exchange assembly.

2. The fluid pump as claimed in claim 1, wherein the motor is a pneumatically actuated motor having a motor housing that defines a motor gas inlet and a motor gas outlet, wherein the motor gas outlet is fluidly connected to the venturi inlet opening.

3. The fluid pump as claimed in claim 2, further comprising a compressed fluid source fluidly connected to the gas inlet of the pneumatically actuated motor.

4. The fluid pump as claimed in claim 3, wherein the compressed fluid source is an E-size oxygen cylinder.

5. The fluid pump as claimed in claim 2, further comprising a speed reducer connected to the motor shaft between the motor shaft and the gas exchange assembly.

6. The fluid pump as claimed in claim 1, wherein the motor is electrically actuated.

7. The fluid pump as claimed in claim 6, further comprising rechargeable batteries electrically connected to the motor.

8. The fluid pump as claimed in claim 1, further comprising a compressed fluid source fluidly connected to the venturi inlet opening.

9. The fluid pump as claimed in claim 1, wherein the gas exchange assembly comprises a housing that defines a blood inlet and a blood outlet, a fiber-based distributor disk surrounded by the housing, a double lumen shaft connected to the fiber-based distributor disk, and a gas plenum connected to the double lumen shaft.

10. A portable pump used to pump liquid blood during patient transports, the portable pump comprising:

a pneumatically actuated motor that defines a motor gas inlet and a motor gas outlet, the pneumatically actuated motor further comprising a motor shaft;

a venturi defining a venturi inlet opening, a venturi exhaust opening, and a venturi suction opening, with the venturi inlet opening fluidly connected to the motor gas outlet; and a gas exchange assembly connected to the motor shaft.

11. The portable pump as claimed in claim 10, wherein the venturi suction opening is fluidly connected to the gas exchange assembly.

12. The portable pump as claimed in claim 10, wherein the gas exchange assembly further comprises a double lumen shaft that defines a shaft inlet, wherein the motor gas outlet is fluidly connected to the shaft inlet.

13. The fluid pump as claimed in claim 10, further comprising a speed reducer connected to the motor shaft between the motor shaft and the gas exchange assembly.

14. The fluid pump as claimed in claim 10, further comprising a compressed fluid source fluidly connected to the gas inlet of the pneumatically actuated motor.

15. The fluid pump as claimed in claim 10, wherein the compressed fluid source is an E-size oxygen cylinder.

16. The fluid pump as claimed in claim 10, wherein the gas exchange assembly comprises a housing that defines a blood inlet and a blood outlet, a fiber-based distributor disk surrounded by the housing, a double lumen shaft connected to the fiber-based distributor disk, and a gas plenum connected to the double lumen shaft.

* * * * *